United States Patent [19]

Johansson

[11] Patent Number: 5,464,440
[45] Date of Patent: Nov. 7, 1995

[54] POROUS IMPLANT WITH TWO SETS OF PORES

[75] Inventor: Thomas Johansson, Höganäs, Sweden

[73] Assignee: LuCoCer Aktiebolag, LuleA, Sweden

[21] Appl. No.: 244,323

[22] PCT Filed: Nov. 13, 1992

[86] PCT No.: PCT/SE92/00784

§ 371 Date: May 18, 1994

§ 102(e) Date: May 18, 1994

[87] PCT Pub. No.: WO93/13815

PCT Pub. Date: Jul. 22, 1993

[30] Foreign Application Priority Data

Jan. 13, 1992 [SE] Sweden ................................. 9200072

[51] Int. Cl.⁶ ............................................ A61F 2/28
[52] U.S. Cl. ............................. 623/16; 623/11; 623/13; 623/15
[58] Field of Search ............................. 623/11, 13, 15, 623/16

[56] References Cited

U.S. PATENT DOCUMENTS

| | | | |
|---|---|---|---|
| 4,440,750 | 4/1984 | Glowacki et al. | 623/11 |
| 4,542,539 | 9/1985 | Rowe, Jr. et al. | 623/16 |
| 4,629,464 | 12/1986 | Takata et al. | 623/16 |
| 4,713,076 | 12/1987 | Draenert | 623/16 |
| 4,778,471 | 10/1988 | Bajpai | 623/11 |
| 4,957,509 | 9/1990 | Tamari et al. | |
| 5,073,114 | 12/1991 | Detsch | 623/16 |
| 5,164,187 | 11/1992 | Constantz et al. | 623/16 |

FOREIGN PATENT DOCUMENTS

| | | |
|---|---|---|
| 0267624 | 5/1988 | European Pat. Off. . |
| 3717818C2 | 1/1992 | Germany . |
| WO92/21302 | 12/1992 | WIPO . |

*Primary Examiner*—Paul Prebilic
*Attorney, Agent, or Firm*—Nixon & Vanderhye

[57] ABSTRACT

The present invention relates to an implant made of a porous non-toxic material having a total open porosity exceeding 5% by volume but not exceeding 80% by volume within at least one portion of the implant, which is characterized in that: communicating micropores, having a size of less than or equal to 10 µm, make up not more than 10% of the total pore volume in said at least one portion of the implant; and at least 5% of at least one section of the surface on the implant is covered by substantially evenly distributed pores having a pore size exceeding 50 µm.

20 Claims, No Drawings

POROUS IMPLANT WITH TWO SETS OF PORES

TECHNICAL FIELD

The present invention relates to the field of medical technology and more specifically to the field of implantology, and relates to implants made of a porous, non-toxic material having a total open porosity exceeding 5% by volume but not exceeding 80% by volume within at least a portion of the implant.

BACKGROUND ART

When implant materials are used and are subjected to a substantial mechanical load, a high strength is the primary requirement. This is achieved by using essentially conventional construction materials—e.g. stainless steel, cobalt-chromium alloys, titanium and titanium-alloys, various ceramic materials such as silicon nitride and polymers. In order to fix implants, it is common practice to utilize a topographical surface or pores. In this connection special requirements as to holding and bone ingrowth must be met. A prior Swedish patent application No. 9101677-4 includes some important new aspects regarding primarily the pore size distribution. Thus, specific and complex pore size distributions can be utilized to accommodate bone ingrowth-promoting agents and to provide a satisfactory bone ingrowth in large pores.

BRIEF DISCLOSURE OF THE INVENTION

The object of the present invention is to provide an improved implant as compared to the implant according to said Swedish patent application No. 9101677-4. The present invention relates more specifically to substantially limiting the porosity of micropores by adding bone ingrowth-promoting agents through carriers, which completely or partially fill micropores as well as pores or cavities in the surface layer, which makes the need of a large available surface less important. Thus, another object of the invention is to improve the bone ingrowth and the healing not only by creating geometrical opportunities for a satisfactory ingrowth but also by allowing a time control of the bone ingrowth, through different concentrations and release of active agents.

Generally, the purpose of the invention is to provide implants having the following characteristics: high strength, excellent biocompatibility by using bone ingrowth-promoting agents deposited in pores or in surface areas for time controlled bone ingrowth in order to achieve an improved reproduceable holding of the implant.

These and other objects of the invention can be achieved therein that communicating micropores, having a size of 10 µm or less, preferably less than 5 µm, most preferably less than 2 µm, make up not more than 10% of the total pore volume, preferably not more than 5% of the total pore volume in said at least one portion of the implant, and that at least 5% of at least one section of the surface of the implant is covered by substantially evenly distributed pores having a pore size exceeding 50 µm preferably in the range of 50–500 µm, more preferably in the range of 75–400 µm, or in the range of 100–300 µm, or in the range of 150–250 µm.

The term pore size is defined, as far as pores having pore sizes smaller than or equal to 50 µm are concerned, as sizes calculated by means of conventional Hg-porosimetry, the relation between the pressure and the pore diameter (2r) being obtained through the expression:

$$p = \frac{2s \cos F}{r},$$

p=the pressure s=the surface tension of Hg for a certain temperature; and

F=the miniscus angle (marginal angle; referens see L. C. Ritter and R. L. Drake, Ind. Eng. Chem. 17 782 (1945))

Pore sizes exceeding 50 µm are defined as sizes obtained through an optical measurement in a light microscope on a cross section of the specimens in a section made at a depth of 0.1 µm and in a section perpendicular to the surface of the specimen, respectively.

The larger pores preferably are limited to, i.e. exist essentially only in the surface layer, more particularly are limited to a surface layer having a thickness of 3 mm, preferably 2 mm and suitably 0.3 mm. If for the rest the porosity is limited to a microporosity, i.e. to pores not larger than 10 µm in diameter and having a total volume of micropores of not more than 10%, a high strength can be maintained.

In the pores one or several of those agents, which include bone-promoting agents, agents for bone growth or bone ingrowth, are deposited before the implantation, which agents can be included in a carrier, which can be made of a polymer, a hydrogel or the like. The bone ingrowth promoting agents can be insulin-like growth factor (IGF), platelet-derived growth factor (PDFG), bone morphogenetic protein (BMP), or transforming growth factor (TGF). Additionally, antibiotics, calcium phosphate compounds, fluoride compounds, or hyaluronic acid can be used. Due to the fact that the pores can be completely filled with the carrier and the included active agents, which both of them will successively be released, pores will gradually be available for bone ingrowth. In this way various profiles for the bone ingrowth can be achieved by means of suitable concentration levels and distributions of active agents. Also, the release rate can be controlled by selecting carriers having different degrees of solubility. Different carriers can be used in different layers and/or in different parts of the implant in order to obtain an optimal ingrowth, e.g. a fast initial ingrowth (increased short-time release) designed to provide a quick holding and subsequently a slower ingrowth designed to provide a denser and stronger bone tissue.

Additional aspects and characteristic features of the present invention are set forth in the accompanying claims.

I claim:

1. An implant made of a porous non-toxic material having an outer surface, said porous non-toxic material having a total open porosity exceeding 5% by volume but not exceeding 80% by volume within at least one portion of the implant;

said at least one portion having communicating micropores with a size not larger than 10 µm but greater than 0 µm and making up not more than 10% but greater than 0% of the total pore volume in said at least one portion of the implant;

at least 5% of at least one section of said surface of the implant being covered by substantially evenly distributed pores having a pore size exceeding 50 µm, said pores existing only in a surface layer of the implant;

said micropores together with said pores existing only in said surface layer being completely or partially filled with a substance having a desirable medical or biological function.

2. An implant according to claim 1, wherein said micropores have a size less than 5 µm.

3. An implant according to claim 2, wherein the size of said micropores is less than 2 µm.

4. An implant according to claim 1, wherein said communicating micropores make up not more than 5% of said total pore volume.

5. An implant according to claim 1, wherein the surface within said at least one section of the implant is covered by pores having a diameter size in the range of 50–500 µm.

6. An implant according to claim 1, wherein in a main portion of said at least one section, said pores have a diameter size within the range of 75–400 µm.

7. An implant according to claim 1, wherein in a main portion of said at least one section, said pores have a diameter size within the range of 100–300 µm.

8. An implant according to claim 1, wherein in a main portion of said at least one section, said pores have a diameter size within the range of 150–250 µm.

9. An implant according to claim 1, wherein said surface layer has a thickness of 3 mm.

10. An implant according to claim 1, wherein said surface layer has a thickness of 2 mm.

11. An implant according to claim 1, wherein said surface layer has a thickness of 0.3 mm.

12. An implant according to claim 1, wherein said at least one portion of the implant is made of a material selected from the group consisting of calcium phosphate materials, titanium, cobalt-chromium-alloys, stainless steel, ceramics and polymers.

13. An implant according to claim 12, wherein said ceramic is silicon nitride.

14. An implant according to claim 1, wherein said substance having a desirable medical or biological function is a bone ingrowth-promoting agent.

15. An implant according to claim 14, wherein said bone ingrowth promoting agent is selected from the group consisting of insulin-like growth factor, platelet-derived growth factor, bone-morphogenetic protein, and transforming growth factor.

16. An implant according to claim 1, wherein said substance having a desirable medical or biological function is an antibiotic.

17. An implant according to claim 1, wherein said substance having a desirable medical or biological function is a calcium phosphate compound or a fluoride.

18. An implant according to claim 1, wherein said substance having a desirable medical or biological function is hyaluronic acid.

19. An implant according to claim 1, wherein said substance having a desirable medical or biological function is in a hydrogel, or in a polymer carrier.

20. An implant according to claim 1, wherein said substance having a desirable medical or biological function is differentially deposited in different zones in order to control bone growth rate and bone tissue quality.

* * * * *